(12) United States Patent
Proctor et al.

(10) Patent No.: US 7,057,064 B2
(45) Date of Patent: Jun. 6, 2006

(54) CONTINUOUS PROCESS FOR THE ENANTIOSELECTIVE CATALYTIC HYDROGENATION OF β-KETOESTERS

(75) Inventors: Lee David Proctor, Maeshafn (GB); Anthony John Warr, Chester (GB)

(73) Assignee: Phoenix Chemicals Limited (GB)

( * ) Notice: Subject to any disclaimer, the term of this patent is extended or adjusted under 35 U.S.C. 154(b) by 0 days.

(21) Appl. No.: 10/515,273

(22) PCT Filed: May 21, 2003

(86) PCT No.: PCT/GB03/02192

§ 371 (c)(1),
(2), (4) Date: Nov. 19, 2004

(87) PCT Pub. No.: WO03/097569

PCT Pub. Date: Nov. 27, 2003

(65) Prior Publication Data

US 2005/0154225 A1    Jul. 14, 2005

(30) Foreign Application Priority Data

May 22, 2002    (GB)    .................................... 0211716

(51) Int. Cl.
*C07C 69/66*    (2006.01)
(52) U.S. Cl. ..................................................... 560/179
(58) Field of Classification Search ................. 560/179
See application file for complete search history.

(56) References Cited

U.S. PATENT DOCUMENTS

| 5,508,435 | A |   | 4/1996 | Armstrong, III |         |
| 6,646,135 | B1 | * | 11/2003 | Baiker et al. | 549/319 |

FOREIGN PATENT DOCUMENTS

| EP | 0 295 109 A1 | 12/1988 |
| EP | 1 052 240 A1 | 11/2000 |
| WO | WO 98/04543 A1 | 2/1998 |
| WO | WO 00/29370 A1 | 5/2000 |

OTHER PUBLICATIONS

PCT International Search Report, International Application No. PCT/ GB 03/ 02192, Applicant: Phoenix Chemicals Limited.

(Continued)

*Primary Examiner*—Paul A. Zucker
(74) *Attorney, Agent, or Firm*—Brooks Kushman P.C.

(57) ABSTRACT

The present invention relates to a continuous process for the enantioselective catalytic hydrogenation of β-ketoesters comprising providing a catalytic hydrogenation zone and maintaining it under conditions of temperature and pressure effective for the catalytic hydrogenation of β-ketoesters; continuously supplying to the catalytic hydrogenation zone a substrate comprising a β-ketoester to be hydrogenated, a catalyst effective for enantioselective hydrogenation of the β-ketoester and hydrogen; contacting the substrate, the catalyst and the hydrogen in the hydrogenation zone for a residence time effective for at least partial enantioselective catalytic hydrogenation of the β-ketoester; (d) continuously withdrawing from the hydrogenation zone a reaction product mixture comprising enantioselectively hydrogenated β-ketoester, unreacted β-ketoester, catalyst and hydrogen; (e) supplying the reaction product mixture to a separation zone and separating at least some of the enantioselectively hydrogenated β-ketoester from the reaction product mixture; (f) withdrawing the separated enantioselectively hydrogenated β-ketoester as product; and (g) optionally supplying at least part of the remaining material from the separation zone to the hydrogenation zone.

23 Claims, 1 Drawing Sheet

OTHER PUBLICATIONS

Kitamura, M., et al., *A Practical Asymmetric Synthesis Of Carnitine*, Tetrahedron Letters, Elsevier Science Publishers, Amsterdam, NL, vol. 29, No. 13, 1988, pp. 1555-1556, XP001033752.

Noyori, T. Ohkuma, et al., *Asymmetrical Hydrogenation of β-Keto Carboxylic Esters. A Practical, Purely Chemical Access to B-Hydroxy Esters in High Enantiomeric Purity*, J. Am. Chem Soc. 1987, 109, 5856-5858, XP-002253353.

International Preliminary Examination Report, International application No. PCT/GB 03/02192, Applicant: Phoenix Chemicals Limited et al.

Written Opinion, International application No. PCT/GB03/02192, mailed May 22, 2002; Applicant: Phoenix Chemicals Limited et al.

Kitamura, M., et al., *Convenient Preparation Of Binap-Ruthenium(II) Complexes Catalyzing Asymmetric Hydrogenation Of Functionalized Ketones*, Tetrahedron Letters, vol. 32, pp. 4163-4166, 1991, Pergamon Press plc.

Kitamura, M., et al., *A Practical Asymmetric Synthesis of Carnitine*, Tetrahedron Letters, vol. 29, No. 13, pp. 1555-1556, 1988, Pergamon Press plc.

Pavlov, V.A.., et al., *Enantioselective hydrogenation of β-keto esters catalyzed by chiral binaphthylbisphosine ruthenium complexes*, Russian Chemical Bulletin, vol. 49, No. 4, Apr., 2000.

Ager, David, *Reductions of 1,3-dicarbonyl systems with ruthenium-biarylbisphosphine catalysts*, Tetrahedron: Asymmetry, vol. 8, No. 20, pp. 3327-3355, 1997 Elsevier Science Ltd.

\* cited by examiner

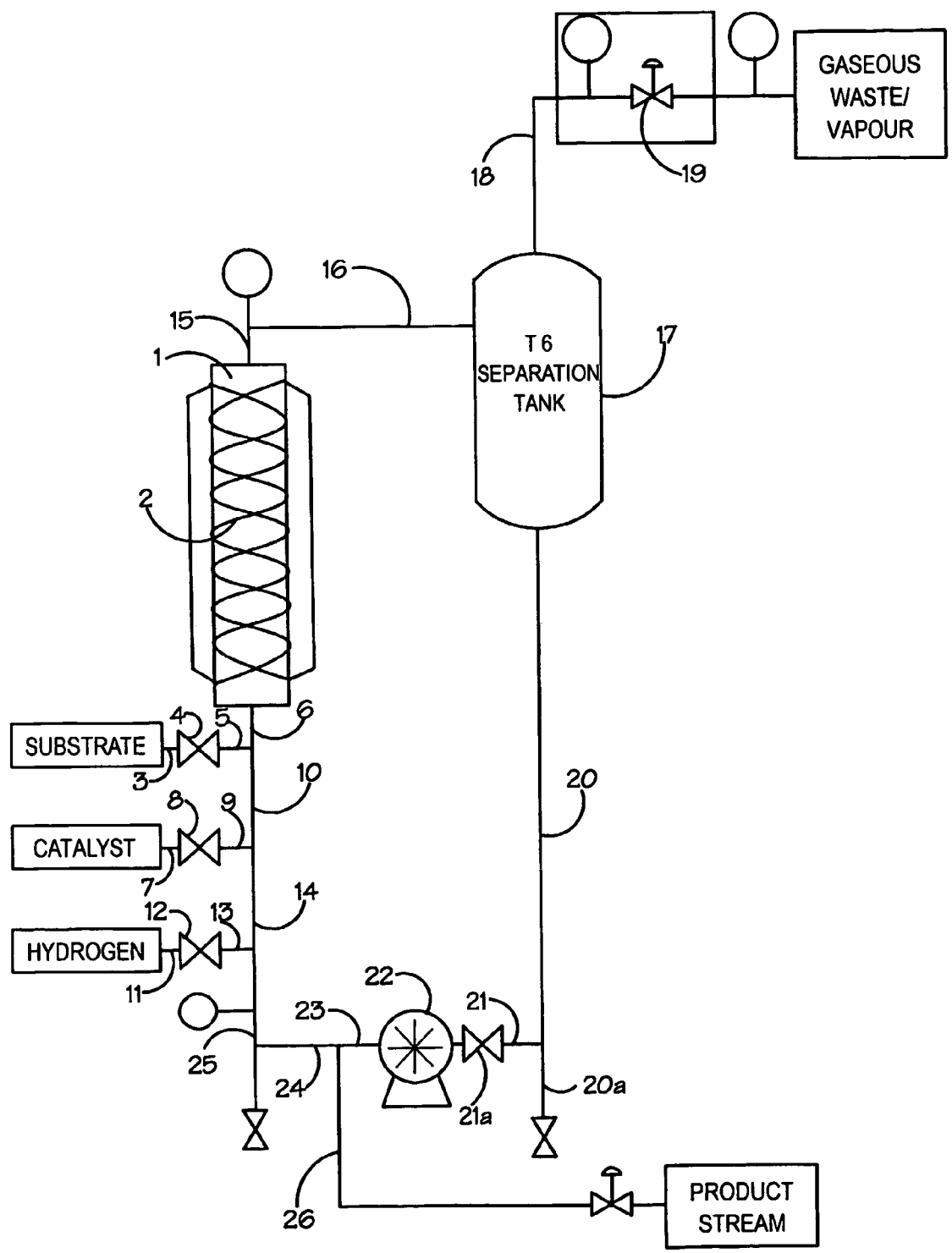

CONTINUOUS PROCESS FOR THE ENANTIOSELECTIVE CATALYTIC HYDROGENATION OF β-KETOESTERS

BACKGROUND OF THE INVENTION

1. Field of the Invention

The present invention concerns a process for the catalytic asymmetric hydrogenation of β-ketoesters.

Useful pharmaceutical intermediates can be formed by the enantioselective hydrogenation of β-ketoesters. The hydrogenation is catalyzed by halogen-containing BINAP-Ru(II) complexes (*Tetrahedron Letters*, Vol. 32, No. 33, pp 4163–4166, 1991). The BINAP ligand (2,2'-bis (diphenylphosphino)-1, 1'-binaphthyl has the formula (1)

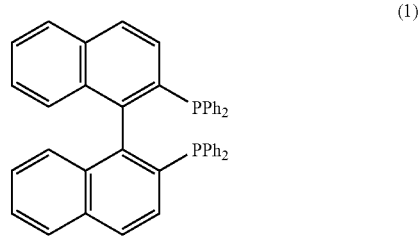

(1)

U.S. Pat. No. 6,162,951 discloses processes for the preparation of BINAP catalysts suitable for use in catalyzing asymmetric hydrogenation reactions. The use of Ru(OCOCH$_3$)$_2$[{S}-BINAP] in the enantioselective hydrogenation of ethyl 4-chloroacetoacetate is reported by Kitamura et al in *Tetrahedron Letters*, Vol. 29, No. 13, pp 1555–1556, 1988. Kitamura et al report that the reaction (scheme A) proceeds within 5 minutes giving the (R)-alcohol in 97% in enantiomeric excess.

2. Background Art

The same reaction was investigated by Pavlov et al in *Russian Chemical Bulletin*, Vol. 49, No. 4, April, 2000, pp 728–731. Pavlov et al studied the effects of the nature of the solvent, the reaction temperature, the pressure, addition of acids, and the reagent ratio on the yield and degree of an enantiomeric enrichment of the reaction products.

A substantial report in connection with reductions of 1,3-dicarbonyl systems with ruthenium-biarylbisphosphine catalysts has been prepared by Ager and Laneman, reported in *Tetrahedron, Asymmetry*, Vol. 8, No. 20, pp 3327–3355, 1997.

EP-A-0295109 teaches a process for preparing an optically active alcohol which comprises a symmetrically hydrogenating a β-keto acid derivative in the presence of a ruthenian-optically active phosphine complex as a catalyst. The resulting alcohol is said to have a high optical purity. Other examples of a symmetric hydrogenation reactions, and catalysts therefor, are disclosed in U.S. Pat. Nos. 5,198,561, 4,739,085, 4,962,242, 5,198,562, 4,691,037, 4,954,644 and 4,994,590.

Although the enantioselective hydrogenation of β-ketoesters has been extensively studied, there has to date been no satisfactory commercial development. In particular, these prior art studies have focussed largely on laboratory scale batchwise processing techniques where there is a requirement for high pressure and high temperature, something which is impractical on a commercial scale. In addition, the prior art processes require low substrate to catalyst ratios (typically in the region 2,000–10,000:1) to achieve a good enatioselectivity. BINAP or other bisaryl bisphosphine-based ligand catalyst are expensive and are often the largest cost in these processes. At low substrate to catalyst ratios, processes are often uneconomic. . . . One such process is described in WO-A-00/29370.

SUMMARY OF THE INVENTION

It is therefore an object of the present invention to provide a commercially satisfactory process for the enantioselective hydrogenation of β-ketoesters. It is a further object of the present invention to provide such a process which may be operated continuously.

According to the present invention, there is provided a continuous process for the enantioselective catalytic hydrogenation of β-ketoesters comprising:

(a) providing a catalytic hydrogenation zone maintained under conditions of temperature and pressure effective for the catalytic hydrogenation of β-ketoesters;

(b) continuously supplying to the catalytic hydrogenation zone a substrate comprising a β-ketoester to be hydrogenated, a catalyst effective for enantioselective hydrogenation of the β-ketoester and hydrogen;

(c) contacting the substrate, the catalyst and the hydrogen in the hydrogenation zone for a residence time effective for at least partial enantioselective catalytic hydrogenation of the β-ketoester;

(d) continuously withdrawing from the hydrogenation zone a reaction product mixture comprising enantioselectively hydrogenated β-ketoester, unreacted β-ketoester, catalyst and hydrogen;

(e) supplying the reaction product mixture to a separation zone and separating at least some of the enantioselectively hydrogenated β-ketoester from the reaction product mixture;

(f) withdrawing the separated enantioselectively hydrogenated β-ketoester as product; and (g) optionally supplying at least part of the remaining material from the separation zone to the hydrogenation zone.

Preferably, the hydrogenation zone is maintained at a pressure of at least about 75 bar, more preferably at least about 90 bar and still more preferably at least about 100 bar. In one preferred process according to the invention, the hydrogenation zone is maintained under conditions of from about 100 to about 150 bar.

The catalytic hydrogenation zone is preferably maintained at a temperature of at least about 75° C., more preferably at least about 90° C. and even more preferably at least about 100° C. In one preferred process according to the invention, the catalytic hydrogenation zone is maintained at a temperature of from about 100 to about 150° C.

The process of the invention may be operated without a solvent. However, in certain processes according to the invention, a solvent may be used. For example, a solvent may be selected from methanol, ethanol/dichloromethane or a mixture of such solvents, for example methanol/dichloromethane. A preferred solvent is ethanol. The β-ketoester is preferably 4-chloroacetoacetate but is suitably of the formula (2):

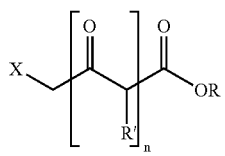

wherein X, R and R' are independently selected from hydrogen, optionally substituted alkyl, aryl, aryl alkyl or alkaryl groups or optionally substituted cyclo alkyl groups; and wherein X may alternatively be selected from fluorine, chlorine, bromine, iodine, mesylates, tosylates, sulphonate esters, tetra alkyl ammonium and other suitable leaving groups;

n is from 1 to 4.

The β-ketoester may have from 1 to 4 keto groups and may, for example, be a β, δ-diketoester.

The catalyst is any catalyst effective for enantioselective hydrogenation of β-ketoesters but is preferably a BINAP or other bisaryl bisphosphine-based ligand catalyst, for example [NH$_2$Et$_2$]$^+$[RuCl{p-MeO-BINAP}$_2${μ-Cl}$_3$]$^-$, [NH$_2$Et$_2$]$^+$RuCl(p-MeO-BINAP)$_2$(μ-Cl)$_3$], [RuI(p-cymene) (p-MeO-BINAP)], [RuI(p-cymene)(p-Tol-BINAP)]I, [RuI (p-cymene)(m-Tol-BINAP)]I, [RuI(p-cymene) (3,5-(t-Bu)$_2$- BINAP)]I, [RuI(p-cymene)(p-Cl-BINAP)]I, [RuI(p-cymene)(p-F-BINAP)]I, [RuI(p-cymene)(3,5-(Me)$_2$- BINAP)]I, [RuI(p-cymene)(H$_8$-BINAP)]I, [RuI(p-cymene) (BIMOP)]I, [RuI(p-cymene)(FUMOP)]I, [RuI(p-cymene) (BIFUP)]I, [RuI(p-cymene)(BIPHEM)]I, [RuI(p-cymene) (MeOl-BIPHEP)]I, [RuCl$_2$(tetraMe-BITIANP)(DMF)$_n$], [RuCl$_2$(BITIANP)(DMF)$_n$], [RuBr$_2$(BIPHEMP)], [RuBr$_2$ (MeO-BIPHEMP)], [RuCl$_2$(BINAP)]$_2$(MeCN), [RuCl$_2$(p-TolBINAP)]$_2$(MeCN), [RuCl$_2$(MeO-BIPHEP)]$_2$(MeCN), [RuCl$_2$(BIPHEP)]$_2$(MeCN), [RuCl$_2$(BIPHEMP)]$_2$, or [Ru (η$^3$-2-Me-allyl)$_2$(MeO-BIPHEP)] or a combination of two or more thereof.

The process of the invention is particularly useful for manufacturing intermediate compounds which may be used to make Statin drugs such as Atorvastatin (Lipitor), Fluvastatin (Lescol) and Rosuvastatin (Crestor). Existing methods for manufacturing the asymmetric unit in such drugs are described, for example, in WO-A-98/04543, U.S. Pat. No. 5,292,939 and U.S. Pat. No. 6,114,566.

Preferably, the residence time in the hydrogenation zone is less than about 30 minutes, more preferably less than about 15 minutes, still more preferably less than about 10 minutes and most preferably less than about 5 minutes.

The inventors have discovered that speed of reaction plays a fundamental role in the selective catalytic hydrogenation of beta-ketoesters. Long reaction times lead to the breakdown of the substrate into acid impurities which can adversely affect the catalyst performance, giving poorer enantioselectivity, lower substrate to catalyst ratio and lead to the formation of unwanted impurities in the chemistry. Excesses of hydrogen and/or extended reaction times can also break down the catalyst into Tu$^0$ which further facilitates achiral reduction giving lower enantioselectivity and a lower substrate to catalyst ratio.

The asymmetric reduction chemistry is limited by the speed at which hydrogen can be provided to the reaction. The rapid provision of hydrogen to the reaction gives improvement in product quality, improvement in enantioselectivity and significantly higher substrate to catalyst ratios. Consequently, there is often a desire to operate at high pressure and/or high temperature.

Through the adoption of a continuous process in accordance with the invention the reaction conditions and stoichiometry of reagents can be carefully controlled to provide significant advantages over prior art batch processes.

This results in a process (according to the invention) which is able to provide a higher quality product at higher yield with higher substrate to catalyst ratio at higher enantiomeric excess than has hitherto been practically possible, at least in commercial scale processing.

A key requirement in the manufacture of asymmetrically hydrogenated β-ketoesters is the so-called "enantiomeric excess" in the product of the desired enantiomer over the non-desired enantiomer. In the process of the invention, the enantiomeric excess in the product is preferably greater than about 95%, more preferably greater than about 96%, yet more preferably greater than about 97% and most preferably greater than about 98%, for example about 99% or more.

In the process of the invention, the substrate/catalyst molar ratio in the hydrogenation zone is preferably at least about 15,000:1, more preferably at least about 20,000:1, even more preferably at least about 30,000:1 and most preferably at least about 40,000:1, for example 50,000:1 or more. Substrate/catalyst molar ratios of up to about 65,000: 1, or even higher, may also be contemplated in the process of the invention.

BRIEF DESCRIPTION OF THE DRAWINGS

The process of the invention will now be more particularly described with reference to the following drawing in which:

FIG. 1 represents a schematic diagram of a simplified plant constructed and arranged to operate in accordance with the process of the invention.

DETAILED DESCRIPTION OF THE PREFERRED EMBODIMENTS

Referring to FIG. 1, there is shown a catalytic hydrogenation reactor 1 which, in this arrangement, is of hastalloy construction. Reactor 1 is surrounded with heating coils 2 for maintaining the reactor as a temperature effective for enantioselective catalytic hydrogenation of β-ketoester.

In the process of the invention a substrate is provided via line 3, flow controller 4 and lines 5 and 6 to reactor 1. The stream in line 6 is joined by a catalyst stream which comes via line 7, flow controller 8 and lines 9 and 10 and by a hydrogen containing stream which comes via line 11, flow controller 12 and lines 13 and 14.

In this example, the substrate is ethyl 4-chloroacetoacetate, the catalyst is R-[RuCl$_2${BINAP}]$_n$ and the hydrogen containing stream supplied in lines 11, 13, 14, 10 and 6 is supplied at a partial pressure sufficient to maintain the partial pressure of hydrogen in reactor 1 at 100 bar. Reactor 1 is maintained at a temperature of 100° C.

The starting materials are fed continuously to reactor 1, the residence time in reactor 1 being sufficient to achieve hydrogenation of ethyl 4-chloroacetoacetate to (S)-ethyl 4-chloro-3-hydroxybutyrate. The reaction product mixture is continuously withdrawn from reactor 1 in line 15 and is passed through line 16 in to separation tank 17. Hydrogen pressure is relieved in line 18 and through pressure control valve 19, along with any unwanted gaseous waste products.

The reaction product mixture goes on in line 20 and, when the reactor is operated as a plugged flow reactor, is recovered in line 20a since valve 21a will be closed in this arrangement. When the reactor is operated as a continuous loop reactor, the reaction product mixture passes on in line 21 through open valve 21a and recycle pump 22 and is recycled to line 14 in lines 23, 24 and 25. A product stream is extracted in line 26.

It will be appreciated that the configuration of plant, pipework, control valves, pumps, release valves, flow controllers and other items of standard equipment shown are illustrated by way of example only and that the process of the invention is not limited to the schematic configuration of plant shown in FIG. 1.

The plant illustrated in FIG. 1 was used in a continuous hydrogenation process as described in the following Examples.

EXAMPLE 1 (COMPARATIVE)

A 600 ml stainless steel Parr reactor was charged with ethanol (340 ml) and ethyl-4-chloroacetoacetate (53 g). The reactor agitator was started and the speed set to 600 rpm. The reactor was pressurised using nitrogen to 7 bar and stirring continued for 5 minutes. After 5 minutes the reactor was slowly vented to ambient pressure, the pressurisation/depressurisation cycle was repeated for a total of five times to ensure complete removal of dissolved oxygen. At the end of the last cycle the reactor set-point temperature was adjusted to 95° C. (R)-[$RuCl_2$(BINAP)]$_n$ catalyst was accurately weighed (23 mg) into a catalyst transfer vessel and the vessel then purged using nitrogen for 5 minutes. The catalyst was flushed from the transfer vessel using deoxygenated solvent into a 100 ml stainless steel injection bomb which was attached to the Parr reactor. When the Parr reactor temperature was between 95° C. and 100° C. the injection bomb was pressurised to 100 bar using hydrogen. Appropriate valves were then opened to transfer the catalyst mixture and hydrogen into the reactor. The contents of the reactor were stirred at 600 rpm for 30 minutes before being cooled to less than 30° C. The reactor was then slowly vented to ambient pressure. The reactor contents were transferred into a 1 L rotary film evaporator flask and the mixture evaporated to constant weight by application of vacuum and by using a heated water bath. The residue was subjected to pot to pot distillation under vacuum to afford a clear colourless oily liquid product of ethyl (S)-(−)-4-chloro-3-hydroxybutyrate in >98% yield, >98% purity and 94% enantiomeric excess.

EXAMPLE 2

A feed tank was charged with 3.6 L ethanol solvent. The solvent was deoxygenated by pumping it through a spray nozzle whilst pressurising to 7 bar with nitrogen and then depressurising through a needle valve at a controlled rate. The pressurisation/depressurisation cycle was repeated three times and the entire process automated using a PLC-based control system. In a similar manner a second feed tank was charged with ethyl-4-chloroacetoacetate (3.6 L) and deoxygenated using the same protocol to that described above. The catalyst, (R)-[$RuCl_2$(BINAP)]$_n$ (149 mg) was charged into a transfer vessel and the vessel purged using nitrogen before transferring the catalyst into the solvent feed tank. The catalyst solution had a concentration of 52.2 mg/Kg.

The two feed systems were connected to the continuous hydrogenation reactor system via two high-pressure pumps. The continuous hydrogenation reactor system was constructed of Hastalloy 276 and comprised a number of in-line static mixers to give a residence time of between 30 and 35 seconds. The static mixers also ensured good mixing of the process streams and rapid absorption of hydrogen. The reactor system was equipped with a recycle pump and an in-line valve which enabled operation as either a plug flow reactor (PFR, valve closed) or a continuous loop reactor (CLR, valve open). The system was equipped with a gas/liquid separator and the liquid level inside the separator controlled using a differential pressure sensor, which in turn operated an exit flow control valve. The reactor system was controlled using a PLC based control system. The hydrogenation reactor was pressurised using hydrogen and the pressure maintained between 90 and 100 bar by continually feeding hydrogen through a mass flow controller at a rate of 2.7 g/h. The reaction liquors passed through a heat exchanger using a pump such that the process temperature was maintained between 102° C. and 105° C.

The system above was operated as a plug flow reactor. The flow rate of the ethyl-4-chloroacetoacetate was set to 2.6 ml/minute and the flow rate of the catalyst solution set to 8.9 ml/min. These flows gave a process concentration of 30% w/w and a substrate to catalyst ratio of 20,000:1.

Over a series of continuous runs, each varying between 4 and 8 hours, the reactor consistently converted >99% ethyl-4-chloroacetoacetate to (S)-ethyl-4-chloro-3-hydroxybutyrate which was isolated after removing the solvents by evaporation to give a chemical yield of >98% and an enantiomeric excess of 98–99%.

EXAMPLE 3

The reactor was set up as Example 2, except it was operated as a continuous loop reactor. The flow rate of the ethyl-4-chloroacetoacetate was set to 2.55 ml/minute and the flow rate of the ethanol catalyst solution set to 6.60 ml/min at a catalyst concentration of 45.8 mg/kg. These flows gave a process concentration of 37% w/w and a substrate to catalyst ratio of 65,000:1.

Over a series of continuous runs, each varying between 4 and 8 hours, the reactor consistently converted >99% ethyl-4-chloroacetoacetate to (S)-ethyl-4-chloro-3-hydroxybutyrate which was isolated after removing the solvents by evaporation to give a chemical yield of >98% and an enantiomeric excess of 98–99%.

EXAMPLE 4 (COMPARATIVE)

A 600 ml stainless steel Parr reactor was charged with ethanol (340 ml) and 6-chloro-3,5-dioxo-hexanoic acid tert-butyl ester (76 g). The reactor agitator was started and the speed set to 600 rpm. The reactor was pressurised using nitrogen to 7 bar and stirring continued for 5 minutes. After 5 minutes the reactor was slowly vented to ambient pressure, the pressurisation/depressurisation cycle was repeated for a total of five times to ensure complete removal of dissolved oxygen. At the end of the last cycle the reactor set-point temperature was adjusted to 95° C. (R)-[$RuCl_2$(BINAP)]n catalyst was accurately weighed (23 mg) into a catalyst transfer vessel and the vessel then purged using nitrogen for 5 minutes. The catalyst was flushed from the transfer vessel using deoxygenated solvent into a 100 ml stainless steel injection bomb which was attached to the Parr reactor. When the Parr reactor temperature was between 95° C. and 100° C. the injection bomb was pressurised to 100 bar using hydrogen. Appropriate valves were then opened to transfer the catalyst mixture and hydrogen into the reactor. The contents of the reactor were stirred at 600 rpm for 40–45 minutes before being cooled to less than 30° C. The reactor was then slowly vented to ambient pressure. The reactor contents were transferred into a 1 L rotary film evaporator flask and the mixture evaporated to consent weight by application of vacuum and by using a heated water bath. The residue was subjected to pot to pot distillation under vacuum to afford a clear colourless oily liquid product of 3R,5S-6-chloro-3,5-dihydroxy-hexanoic acid tert-butyl ester in >95% yield, 90% purity and 93% enantiomeric excess.

EXAMPLE 5

A feed tank was charged with 3.6 L ethanol solvent. The solvent was deoxygenated by pumping it through a spray nozzle whilst pressurising to 7 bar with nitrogen and then depressurising through a needle valve at a controlled rate. The pressurisation/depressurisation cycle was repeated three times and the entire process automated using a PLC-based control system. In a similar manner a second feed tank was charged with 6-chloro-3,5-dioxo-hexanoic acid tert-butyl ester (3.6 L) and deoxygenated using the same protocol to that described above. The catalyst, (R)-[RuCl$_2$(BINAP)]$_n$ (150 mg) was charged into a transfer vessel and the vessel purged using nitrogen before transferring the catalyst into the solvent feed tank. The catalyst solution had a concentration of 52.6 mg/Kg.

The two feed systems were connected to the continuous hydrogenation reactor system via two high-pressure pumps. The continuous hydrogenation reactor system was constructed of Hastalloy 276 and comprised a number of in-line static mixers to give a residence time of between 30 and 35 seconds. The static mixers also ensured good mixing of the process streams and rapid absorption of hydrogen. The reactor system was equipped with a recycle pump and an in-line valve which enabled operation as either a plug flow reactor (PFR, valve closed) or a continuous loop reactor (CLR, valve open). The system was equipped with a gas/liquid separator and the liquid level inside the separator controlled using a differential pressure sensor, which in turn operated an exit flow control valve. The reactor system was controlled using a PLC based control system. The hydrogenation reactor was pressurised using hydrogen and the pressure maintained between 90 and 100 bar by continually feeding hydrogen through a mass flow controller at a rate of 2.7 g/h. The reaction liquors passed through a heat exchanger using a pump such that the process temperature was maintained between 102° C. and 105° C.

The system above was operated as a plug flow reactor. The flow rate of the 6-chloro-3,5-dioxo-hexanoic acid tert-butyl ester was set to 3.7 ml/minute and the flow rate of the catalyst solution set to 9.0 ml/min. These flows gave a process concentration of 30% w/w and a substrate to catalyst ratio of 20,000:1.

Over a series of continuous runs, each varying between 4 and 8 hours, the reactor consistently converted >90% 6-chloro-3,5-dioxo-hexanoic acid tert-butyl ester to 3R,5S-6-chloro-3,5-dihydroxy-hexanoic acid tert-butyl ester which was isolated after removing the solvents by evaporation to give a chemical yield of >95% and an enantiomeric excess of 97–98%.

EXAMPLE 6

The reactor was set up as Example 5, except it was operated as a continuous loop reactor. The flow rate of the 6-chloro-3,5-dioxo-hexanoic acid tert-butyl ester was set to 3.7 ml/minute and the flow rate of the ethanol catalyst solution set to 6.73 ml/min at a catalyst concentration of 46.7 mg/kg. These flows gave a process concentration of 37% w/w and a substrate to catalyst ratio of 65,000:1.

Over a series of continuous runs, each varying between 4 and 8 hours, the reactor consistently converted >95% 6-chloro-3,5-dioxo-hexanoic acid tert-butyl ester to 3R,5S-6-chloro-3,5-dihydroxy-hexanoic acid tert-butyl ester which was isolated after removing the solvents by evaporation to give a chemical yield of >95% and an enantiomeric excess of 97–98%.

The invention claimed is:

1. A continuous process for the enantioselective catalytic hydrogenation of β-ketoesters comprising:
   (a) providing a catalytic hydrogenation zone and maintaining it under conditions of temperature and pressure effective for the catalytic hydrogenation of β-ketoesters;
   (b) continuously supplying to the catalytic hydrogenation zone a substrate comprising a β-ketoester to be hydrogenated, a catalyst effective for enantioselective hydrogenation of the β-ketoester and hydrogen;
   (c) contacting the substrate, the catalyst and the hydrogen in the hydrogenation zone for a residence time effective for at least partial enantioselective catalytic hydrogenation of the β-ketoester, the substrate/catalyst molar ratio in the hydrogenation zone being at least about 15,000:1;
   (d) continuously withdrawing from the hydrogenation zone a reaction product mixture comprising enantioselectively hydrogenated β-ketoester, unreacted β-ketoester, catalyst and hydrogen;
   (e) supplying the reaction product mixture to a separation zone and separating at least some of the enantioselectively hydrogenated β-ketoester from the reaction product mixture;
   (f) withdrawing the separated enantioselectively hydrogenated β-ketoester as product; and
   (g) optionally supplying at least part of the remaining material from the separation zone to the hydrogenation zone.

2. A process according to claim 1, wherein the hydrogenation zone is maintained at a pressure of at least 75 bar.

3. A process according to claim 2, wherein the hydrogenation zone is maintained under pressure conditions of from 100 to 150 bar.

4. A process according to claim 1, wherein the residence time in the hydrogenation zone is less than 30 minutes.

5. A process according to claim 4, wherein the residence time in the hydrogenation zone is less than 15 minutes.

6. A process according to claim 1, wherein the hydrogenation zone is maintained at a temperature of at least 75° C.

7. A process according to claim 6, wherein the hydrogenation zone is maintained at a temperature of from 100 to 150° C.

8. A process according to claim 1, wherein the β-ketoester has the formula (2):

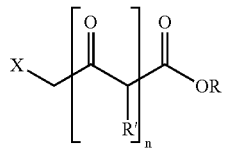

(2)

wherein R, R' and X are independently selected from hydrogen, optionally substituted alkyl, aryl, aryl alkyl or alkaryl groups or optionally substituted cyclo alkyl groups; and wherein X may alternatively be selected from fluorine, chlorine, bromine, iodine, mesylates, tosylates, sulphonate esters, tetra alkyl ammonium and other suitable leaving groups; or X=R; and n is from 1 to 4.

9. A process according to claim 1, wherein the catalyst is selected from the group consisting of a BINAP and other bisaryl bisphosphine based ligand catalysts and mixtures thereof.

10. A process according to claim 2, wherein the residence time in the hydrogenation zone is less than 30 minutes.

11. A process according to claim 3, wherein the residence time in the hydrogenation zone is less than 30 minutes.

12. A process according to claim 10, wherein the residence time in the hydrogenation zone is less than 15 minutes.

13. A process according to claim 11, wherein the residence time in the hydrogenation zone is less than 15 minutes.

14. A process according to claim 2, wherein the hydrogenation zone is maintained at a temperature of at least 75° C.

15. A process according to claim 3, wherein the hydrogenation zone is maintained at a temperature of at least 75° C.

16. A process according to claim 4, wherein the hydrogenation zone is maintained at a temperature of at least 75° C.

17. A process according to claim 5, wherein the hydrogenation zone is maintained at a temperature of at least 75° C.

18. A process according to claim 2, wherein the hydrogenation zone is maintained at a temperature of from 100 to 150° C.

19. A process according to claim 3, wherein the hydrogenation zone is maintained at a temperature of from 100 to 150° C.

20. A process according to claim 4, wherein the hydrogenation zone is maintained at a temperature of from 100 to 150° C.

21. A process according to claim 5, wherein the hydrogenation zone is maintained at a temperature of from 100 to 150° C.

22. A process according to claim 1 wherein the process of withdrawing in step (f) produces an enantiomeric excess greater than 95%.

23. The process of claim 22 wherein the enantiomeric excess is 98–99%.

* * * * *